(12) United States Patent
Osypka

(10) Patent No.: US 10,207,088 B2
(45) Date of Patent: Feb. 19, 2019

(54) MONITORING AND REGULATION DEVICE CONFIGURED FOR MONITORING AND REGULATING CARDIAC PARAMETERS

(71) Applicant: Peter Osypka, Grenzach-Wyhlen (DE)

(72) Inventor: Peter Osypka, Grenzach-Wyhlen (DE)

(73) Assignee: Peter Osypka, Grenzach-Wyhlen (DE)

( * ) Notice: Subject to any disclaimer, the term of this patent is extended or adjusted under 35 U.S.C. 154(b) by 280 days.

(21) Appl. No.: 15/138,942

(22) Filed: Apr. 26, 2016

(65) Prior Publication Data

US 2016/0325079 A1 Nov. 10, 2016

(30) Foreign Application Priority Data

May 6, 2015 (EP) .................................... 15020070

(51) Int. Cl.
  *A61B 5/02* (2006.01)
  *A61M 27/00* (2006.01)
  (Continued)

(52) U.S. Cl.
  CPC ......... *A61M 27/006* (2013.01); *A61B 5/0215* (2013.01); *A61B 5/0538* (2013.01);
  (Continued)

(58) Field of Classification Search
  None
  See application file for complete search history.

(56) References Cited

U.S. PATENT DOCUMENTS

| | | | |
|---|---|---|---|
| 6,746,404 B2 * | 6/2004 | Schwartz ............. | A61B 5/0031 128/898 |
| 6,974,436 B1 | 12/2005 | Aboul-Hosn et al. | |

(Continued)

OTHER PUBLICATIONS

Search Report dated Nov. 9, 2015 in connection with EP1502007.7.

*Primary Examiner* — Michael R Bloch
(74) *Attorney, Agent, or Firm* — Locke Lord LLP; Scott D. Wofsy

(57) ABSTRACT

The invention relates to a monitoring and regulation device configured for implantation in the heart, including at least one pressure sensor located in a distally arranged section of a shaft and a regulation device configured for regulating blood flow and blood pressure. The regulation device includes the shaft, a first pressure valve, a second pressure valve, and a sliding element. The pressure sensor is configured to output data that is used to monitor vital parameters of a cardiovascular system. The shaft is tubular with a lumen that extends axially there through. The shaft has distal and proximal sections and a central section, wherein the distal and proximal sections are disc-shaped extended, thus forming a first double disc at the distal section and a second double disc at the proximal section. The central section links the first and second double discs. The central section of the shaft has an opening. The first pressure valve is disposed in the opening in the central section of the shaft. The second pressure valve is located in the lumen in the proximal section of the shaft. The sliding element is housed inside the lumen. The sliding element has an axially movable and rotatable cylindrical piston and a piston rod, wherein pushing the piston towards the distal section of the shaft or rotating the piston results in a partial or complete closing of the opening for controlling the blood flow.

7 Claims, 6 Drawing Sheets

(51) Int. Cl.
*A61M 1/10* (2006.01)
*A61B 5/0215* (2006.01)
*A61B 5/053* (2006.01)
*A61B 5/00* (2006.01)
*A61M 39/22* (2006.01)
*A61N 1/05* (2006.01)
*A61N 1/362* (2006.01)
*A61M 1/12* (2006.01)
*A61B 17/00* (2006.01)

(52) U.S. Cl.
CPC ........... *A61B 5/686* (2013.01); *A61M 1/1086* (2013.01); *A61M 1/1087* (2014.02); *A61M 39/22* (2013.01); *A61N 1/056* (2013.01); *A61N 1/362* (2013.01); *A61B 2017/00575* (2013.01); *A61B 2017/00592* (2013.01); *A61B 2017/00597* (2013.01); *A61B 2017/00606* (2013.01); *A61M 1/101* (2013.01); *A61M 1/1005* (2014.02); *A61M 1/1008* (2014.02); *A61M 1/1081* (2013.01); *A61M 1/12* (2013.01); *A61M 1/127* (2013.01); *A61M 2230/30* (2013.01)

(56) References Cited

U.S. PATENT DOCUMENTS

2002/0173742 A1   11/2002  Keren et al.
2006/0178550 A1*  8/2006  Jenson ................ A61M 1/1053
                                             600/16
2008/0109069 A1    5/2008  Coleman et al.

* cited by examiner

Fig. 1
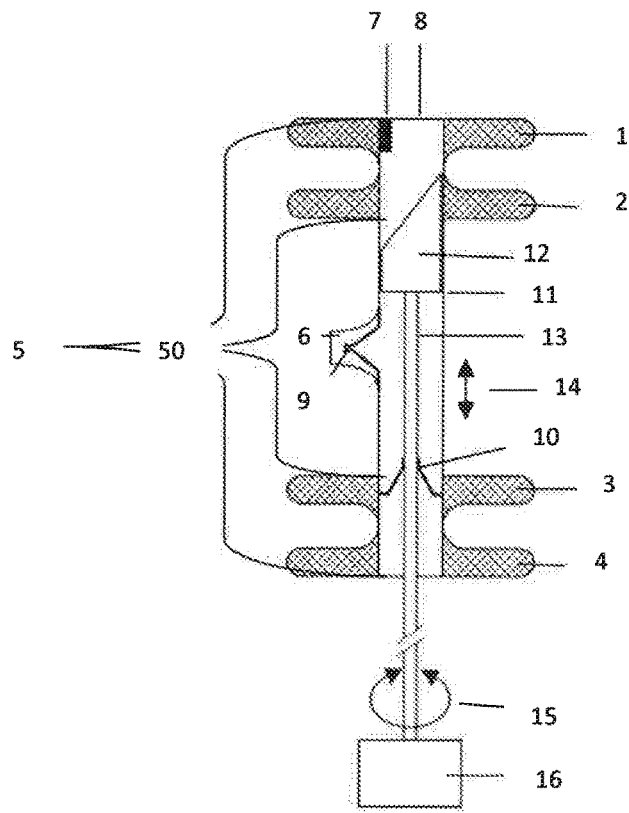
Fig. 1a
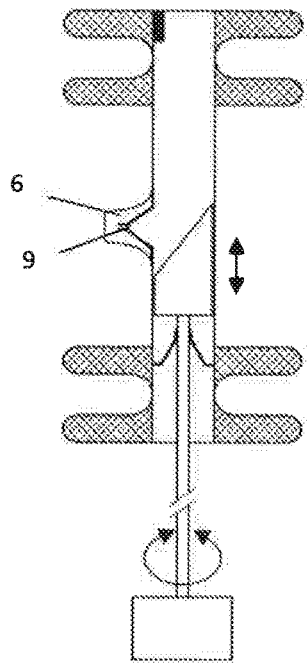
Fig. 1b
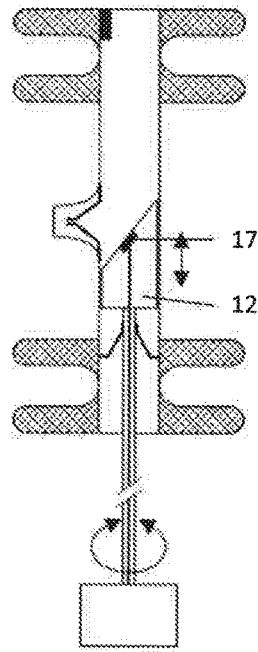
Fig. 1c

MONITORING AND REGULATION DEVICE CONFIGURED FOR MONITORING AND REGULATING CARDIAC PARAMETERS

CROSS-REFERENCE TO RELATED APPLICATIONS

This application claims under 35 U.S.C. 119(a) priority to and benefit of European patent Application No. 15020070.7 filed May 6, 2015 which is incorporated by reference herein in its entirety.

BACKGROUND OF THE INVENTION

1. Field of the Invention

The present invention relates to a monitoring and regulation device which can be used to monitor the vital parameters of the cardiovascular system and can be used to reduce left ventricular diastolic pressure. By means of the inventive device high blood pressure can be treated by influencing the blood flow directly in the heart.

2. Description of Related Art

US Publication US2002/0173742 corresponding to U.S. Pat. No. 8,091,556 describes a method of reducing left atrial pressure in a human with congestive heart failure, the method comprising: providing a shunt configured for percutaneous placement across an atrial septum of the human with congestive heart failure, the shunt having first and second self-expanding end regions configured to retain the shunt within the atrial septum, the shunt including a valve configured to open to permit blood to flow from a left atrium to a right atrium only when the left atrial pressure exceeds a pressure in the right atrium; implanting the shunt transeptally between the left atrium and the right atrium of the heart of the human, such that the first end region communicates with the left atrium and the second end region communicates with the right atrium; and reducing the left atrial pressure by transferring blood from the left atrium to the right atrium through the shunt responsive to a predetermined differential atrial pressure.

U.S. Pat. No. 6,974,436 describes systems and methods for transporting fluid between different locations within a body cavity and, in one particular application, systems and methods for transporting fluids to maintain at least partial blood flow through a protected blood flow path within the right and/or left side of the heart during surgery. The protected blood flow path may be established by positioning one or more conduits within at least a portion of the right and/or left sides(s) of the heart, At least partial blood flow may be maintained through the protected blood flow path by the pumping action of a blood pump disposed within the conduit.

U.S. Pat. No. 7,878,966 corresponding to US20060178550 describes a ventricular assist device to provide cardiac assistance to a damaged ventricle chamber. The ventricular assist device is formed of an ventricle body which is anchorable to spaced ventricle wall portions to provide cardiac assistance. Operation of the ventricular assist device is timed or synchronized with the operating phases of the ventricle chamber. The ventricular assist device can be intravascularly deployed to provide a less invasive treatment procedure and can be adapted to provide static support if active assistance is no longer required.

US20080109069 describes a bypass device, comprising: an implantable hollow flexible conduit configured to be implanted in a human heart, the conduit including first and second ends and a plurality of perforations formed in a sidewall thereof and configured to decrease a pressure of fluid flowing through the conduit; and at least one expandable anchor formed on the conduit and adapted to expand to engage tissue to anchor at least a portion of the conduit to the tissue, the at least one expandable anchor having a plurality of openings formed therethrough and in communication with the hollow conduit such that blood can flow through the plurality of openings and through the hollow conduit.

There remains a need to provide a monitoring and regulation device monitoring cardiac parameters such as blood pressure, heart rate, cardiac output, stroke volume and regulating said parameters in case of deviations from the accepted standards.

SUMMARY OF THE INVENTION

The present invention relates to a monitoring and regulation device configured for implantation in the heart comprising a monitoring device (sensor-monitor system) configured for measuring and monitoring the vital parameters of the cardiovascular and a regulation device configured for regulation of the blood flow and the blood pressure, respectively.

Access is provided to the left ventricle via the right ventricle and the interventricular septum and by inserting a monitoring and regulation device which may re-direct the blood flow from the left ventricle to the right ventricle thus lowering the blood volume in the left ventricle and thus lowering the blood pressure.

The present invention relates to a monitoring and regulation device configured for implantation in the heart comprising:

a monitoring unit configured for measuring and monitoring the vital parameters of the cardiovascular system, said monitoring unit being set to obtain data from at least one pressure sensor (7) being located in the distally arranged part of shaft (5) of the regulation device, and a regulation device configured for regulating the blood flow and the blood pressure, respectively, comprising a fluid-tight tubular shaft (5) with a lumen (8) extending axially there through, with pressure valve (10) and with sliding element (11), said shaft having distal and proximal sections and a central section(50), whereby the distal and proximal sections are disc-shaped extended thus forming a double disc(1) (2) and (3), (4), respectively, and whereby the central section (50) links the distally placed double disc (1), (2) with the proximally placed double disc (3), (4), and whereby the central section (50) of shaft (5) has an opening (6) with pressure valve (9), and whereby the length of the central section (50) is adapted to the anatomical characteristics of the right ventricle, said length corresponding to the distance between myocardium wall of the right ventricle and right ventricle septum; and whereby pressure valve (10) is located in the proximally arranged part of shaft (5); and whereby sliding element (11) consists of an axially movable and rotatable cylindrical piston (12) with piston rod (13), the sliding element being housed inside lumen (8) such that pushing piston (12) towards the distal section of shaft (5) or rotating piston (12) results in a partially or completely closing of opening (6).

The term "disc-shaped" can relate to similar structures like umbrella-shaped, discus-shaped and ellipsoid-shaped. The disc shaped sections (1), (2), (3) and (4), have a larger diameter than the tubular shaft (5). The diameter ratio is approximately 1:3-1:4. The diameter of each disc-shaped section is preferably the same.

The distal part of the tubular shaft with sections (1) and (2) is designed to be implanted into the ventricle septum. The proximal part of the tubular shaft with sections (3) and (4) is designed to be implanted into the myocardium of the right ventricle.

The disc shaped sections (1), (2), (3) and (4) are used for fixing the monitoring and regulation device in the ventricle septum and in the myocardium of the right ventricle, respectively. The diameter of the disc shaped sections is dimensioned such that the device is held in place after implantation and thus slipping is prevented.

The central section (50) has an opening (6) with a one-way pressure valve (9) allowing blood to flow from the left ventricle to the right ventricle and blocking blood to flow back from the right ventricle into lumen (8). The pressure valve might be a silicone valve. Such valves are well known and commercially available. The blood flow from lumen (8) to the chest cavity is prevented by one-way pressure valve (10).

The regulation device is made of biocompatible and flexible materials. Each biocompatible material may be used from which a shaft with lumen and disc shaped extension may be shaped. The device must be foldable in order to be insertable by means of a trocar.

Suitable materials are for instance plastics such as silicone or polyurethane, metals, shape memory plastics or shape memory metals, preferably nitinol. Nitinol wires or strands may be used. The nitinol wires may also be polymer coated or coated with a further metal like gold coated nitinol wires.

In one embodiment the monitoring and regulation device is made of plastic, e.g. made of silicone or polyurethane, preferably silicone.

In a preferred embodiment the monitoring and regulation device is a braiding or mesh made of shape memory metal, preferably nitinol.

Shaft (5) is coated by a fluid tight biocompatible material, preferably by silicone so that no blood can flow from the left ventricle to the right ventricle unintentionally. The blood flow from the left ventricle to the right ventricle takes place in a controlled way. The coating prevents blood from entering into the braiding whereby coagulation of the blood could be initiated. The coating further prevents blood to leave the shaft unintentionally. Moreover, the coating improves the sliding and rotation of the sliding element.

If the monitoring and regulation device consists of a braiding or mesh of nitinol wires coated with silicone, the coating area is provided with a recess forming opening (6). Pressure valve (9) is placed and fixed inside said recess. Opening (6) may also be a small silicone cylinder which is attached to the central section (50) of the monitoring and regulation device.

The sliding element (11) has a tubular or cylindrical piston (12) made e.g. of plastic. The sliding element may also be formed by metal strands or metal coils. The piston (12) is equipped with a piston rod (13). The diameter of the piston corresponds to the diameter of the lumen (8) of shaft (5), said piston thus tightly locking shaft (5). No blood can thus flow to the chest cavity.

The sliding element must be movable and rotatable housed inside lumen (8) of the monitoring and regulating device such that pushing piston (12) towards the distal section of shaft (5) or rotating piston (12) results in a partially or completely closing of opening (6).

In one embodiment piston (12) of the sliding element (11) has a raked surface at its distal end. Due to this raked surface opening (6) may be closed only by rotation of piston (12). Piston rod (13) is connected to steering element (16).

Opening (6) can be totally or partly closed by moving piston (12) longitudinally inside lumen (8) from its proximal section to its distal section or by rotating piston (12). Piston (12) together with piston rod (13) is moved longitudinally or is rotated by the motor of steering unit (16). The blood flow from the left to the right ventricle is controlled by adjusting the size of opening (6).

In one embodiment the sliding element is made of silicone. The piston rod is detachably fixed to the piston. The sliding element may also be controlled manually.

The steering element consists of an electronically controlled linear actuator or of a threaded rod being connected to an electric motor.

The pressure sensor (7) must be placed such that the movement of the sliding element is not affected. The pressure sensor (7) is located in the distally arranged part of shaft (5), preferably at its upper end. The pressure sensor (7) measures the left ventricular blood pressure.

Suitable pressure sensors are commercially available. An appropriate pressure sensor is sensor "HYPER IMS" developed by Osypka AG and Frauenhofer Institut said sensor transmitting the data telemetrically (Technology Review, March 2009, page 16)

Further sensors may be sensors for the telemedical control of blood parameters or sensors for the measurement of temperature, blood glucose, thrombocytes etc. By means of those sensors deviations from the patients' standard values are determined.

Lumen (8) of the monitoring and regulation device allows insertion of electrode leads, connection leads, guiding catheter and other implantable medical devices for example those devices described in PCT/EP2014002915. The international application PCT/EP2014002915 discloses a device providing access to the left ventricle via the right ventricle.

If a left ventricular stimulation is required, at least one stimulation electrode, e.g. screw-in electrode pole (20) with associated connecting lead (40) is inserted via lumen (8) and guided to the left ventricle through valve (10) and piston (12). Suitable valves allowing the insertion of the electrode pole and the connecting leads are commercially available.

Thus a device is provided which after implantation in the heart not only monitors and regulates the blood pressure but also serves for left ventricular stimulation. (FIG. 3)

As shown in FIG. 4 a device can be provided that may be used for measuring the cardiac impedance signals. The cardiac impedance at end-diastole and end-systole is measured and the thus obtained data are used to compute stroke volume. U.S. Pat. No. 6,511,438 Bernstein/Osypka discloses a method for determining an approximate value for the stroke volume and the cardiac output of a person's heart.

Impedance measures the effective "resistance" to current flow through the body by applying a small alternating current. External electrodes e.g. a coil electrode placed on the body or in the chest cavity may be used. (FIG. 5), (FIG. 6). For resistance measurement a sinusoidal alternating current of more than 10 kHz is made to flow between pole (23) and the poles (20) and (21), said poles (20) and (21) being switched parallel. The current intensity is about 3-5 mA.

The pacemaker can be implanted below the abdominal wall or can be located beyond the body.

To manufacture the monitoring and regulation device being a braiding of nitinol wires first a tubular shaft is braided having a circular or oval opening at one end, on the other proximal end the wires end loosely. The braided shaft is tempered followed by shaping the disc shaped sections (1), (2), (3) and (4) as shown in FIG. 1. Said sections may be formed as single mesh or as double mesh.

The proximal wire ends of section (4) are joined together by a linking member, e. g. a capsule or a clip having an opening too so that lumen (8) runs continuously.

The nitinol braiding with disc shaped sections (1) and (2) and the nitinol braiding with disc-shaped sections (3) and (4) can be braided separately and can be connected to each other by welding at the points facing each other as described in WO2012095314.

The braiding of the monitoring and regulation device in inserted in a folded condition by means of a trocar. When the braiding is pushed out of the trocar it unfolds.

The monitoring and regulation device may optionally be used as permanent implant. The braiding can grow into the tissue like the braiding of already known transseptal occluders.

The sliding element closes the heart muscle tightly, so that bleeding is prevented.

THE FIGURES ARE NUMBERED AS FOLLOWS 1,2,3,4 double disc
1,2 distally placed double disc
3,4 proximally placed double disc
5 tubular shaft
6 opening
7 pressure sensor
8 lumen
9, 10 one-way pressure valve
11 sliding element
12 piston
13 piston rod
14, 15 arrow
16 steering element
17 sensor
20, 21 screw-in electrode pole
22 coiled shaped electrode pole
23 braiding forming an indifferent electrode
30 pacemaker
40, 41, 42, 43 connecting lead
50 central section
51 shaft extended
60 introduction device
70 abdominal wall
80 impedance detecting unit

DESCRIPTION OF THE FIGURES

FIG. 1 shows the inventive monitoring and regulation device of the type of a braiding or a mesh of nitinol wires. Piston (12) is shown in a first starting position (FIG. 1a) and in a second position (FIG. 1b)

Figure 2:
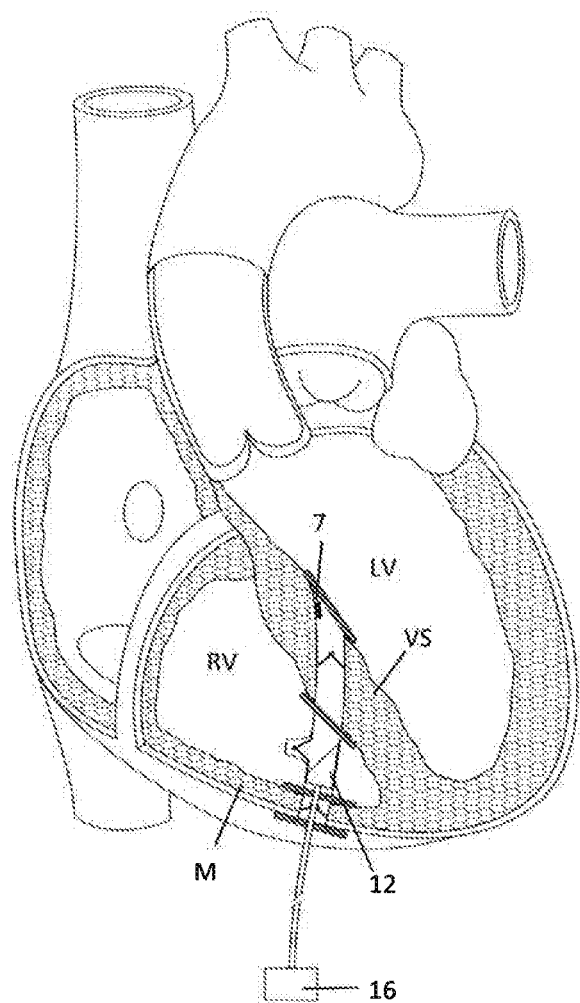

The device comprises a fluid tight tubular shaft (5) braided of nitinol wires and coated by a biocompatible material. Shaft (5) has a lumen (8) extending axially there through with pressure valve (10) and with sliding element (11). Shaft (5) has distal and proximal sections and a central section (50) The distal and proximal sections are disc-shaped extended thus forming a double disc (1) (2) and (3), (4), respectively. The central section (50) links the distally placed double disc (1), (2) with the proximally placed double disc (3), (4). The central section (50) of shaft (5) has an opening (6) with pressure valve (9). The length of the central section (50) is adapted to the anatomical characteristics of the right ventricle (RV), said length corresponding to the distance between myocardium wall of the right ventricle and right ventricle septum. Pressure valve (10) is located in the proximally arranged part of shaft (5). Sliding element (11) consists of an axially movable and rotatable cylindrical piston (12) with piston rod (13), the sliding element being housed inside lumen (8) such that pushing piston (12) towards the distal section of shaft (5) or rotating piston (12) results in a partially or completely closing of opening (6).

A pressure sensor (7) is placed in the distally arranged part of shaft (5) at the upper end of shaft (5), said sensor being configured for measuring the left ventricular blood pressure. Sliding element (11) is connected to steering element (16). Piston (12) is inserted into lumen (8) of shaft (5) and tightly seals shaft (5). In the embodiment shown in FIG. 1 piston (12) comprises a raked surface at its distal end. The longitudinal movement of piston (12) is marked by arrow (14). The rotating movement of piston (12) is marked by arrow (15).

FIG. 1a shows the starting position of piston (12). Piston (12) is distally located above opening (6). After implantation of the monitoring and regulation device the connection between right and left ventricle is sealed by piston (12) in its starting position and by pressure valve (9). There is no blood flow between the right and left ventricle. Pressure valve (10) seals the right ventricle thus preventing any bleeding from the right ventricle to the chest cavity. The blood pressure is measured by sensor (7). If deviations from accepted standards are monitored, steering unit (16) causes piston (12) to move downwards lumen (8) until the position shown in FIG. 1b is reached. Opening (6) to the right ventricle is now free allowing blood to flow into the right ventricle via valve (9) due to the pressure difference between left and right ventricle. Valve (9) is a one way valve allowing the blood to pass in one direction only from the left ventricle (LV) to the right ventricle and blocking the blood flow back from the right ventricle to the lumen of the shaft.

FIG. 1c illustrates a further embodiment of the monitoring and regulation device whereby piston (12) comprises an additional sensor (17) for monitoring blood parameters such as e.g. hemoglobin, thrombocytes, blood sugar and the like. Sensor (17) may also be distally placed in lumen (8).

FIG. 2 illustrates the inventive monitoring and regulation device implanted in the heart. Piston 12) is in its downward position as shown in FIG. 1b. The device of FIG. 1a, 1b is implanted. Reference numbers of FIG. 1a and 1b shall apply. Not all reference numbers are repeated in FIG. 2. The distal section of tubular shaft (5) with double disks (1) and (2) is implanted in the ventricle septum (VS). The proximal section of tubular shaft (5) with double disks (3) and (4) is implanted in the myocardium (M) of the right ventricle. Opening (6) to the right ventricle is free allowing blood to flow from the left ventricle into the right ventricle due to the pressure difference between left and right ventricle thus lowering the blood volume in the left ventricle. If the heart contracts less blood is pumped into the aorta. The systolic blood pressure decreases. The size of opening (6) may be reduced by pushing piston (12) in the distal direction towards the ventricle septum or by rotating piston (12). The necessary size reduction of opening (6) depends on the left ventricular blood pressure data monitored by pressure sensor (7), said size reduction being adjusted by steering element (16). The blood flow from the left ventricle into the right ventricle is thus be controlled by adjusting the size of opening (6).

Figure 3:
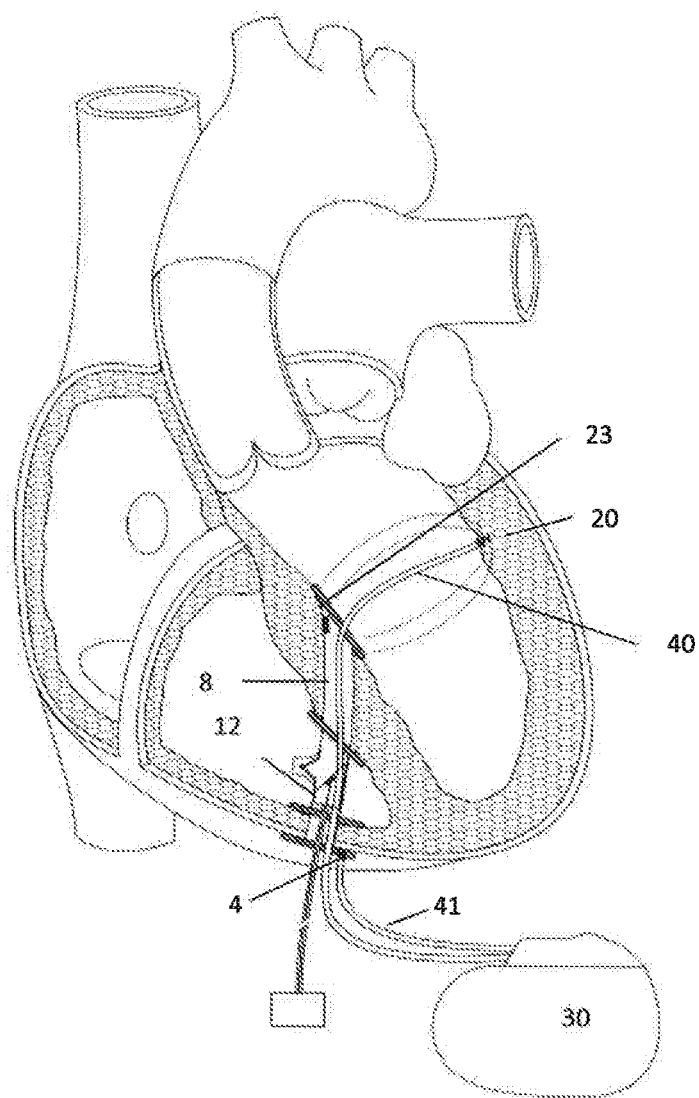

FIG. 3 shows the monitoring and regulation device being implanted in the heart. The device shown in FIG. 3 is in addition used for left ventricular stimulation. Screw-in electrode pole (20) with associated connecting lead (40) is inserted via lumen (8) and guided through valve (10) (not shown) and piston (12). In doing so, the screw-in electrode is guided through the myocardium of the right ventricle and further on through the ventricle septum. The screw-in electrode pole may be fixed in the endocardium of the left ventricle. The screw-in electrode pole (20) is connected to the pacemaker (30) via connecting lead (40), said pacemaker (30) sending an electric stimulation pulse. The proximally placed disc (4) of the nitinol mesh of said monitoring and regulation device is connected to the pacemaker via connecting lead (41). The whole nitinol mesh is thus forming the indifferent pole (23).

The screw-in electrode pole may be unipolar or bipolar. The indifferent reference electrode pole for the unipolar screw-in electrode pole is either the pacemaker housing (30) or the nitinol mesh (23).

Further to the stimulation of the heart the implantable device may measure a cardiac impedance signal. The impedance data are transmitted to an analyzer for calculation of cardiac output.

Figure 4:
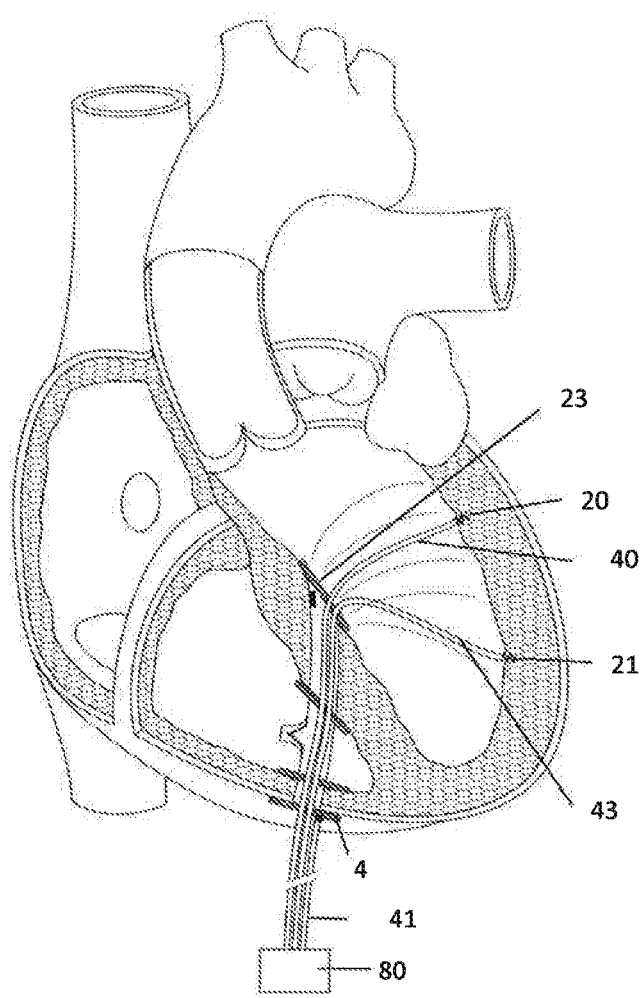

FIG. 4 shows the monitoring and regulation device being implanted in the heart. The device shown in FIG. 4 is in addition used for measuring the cardiac impedance signal. Screw-in electrode poles (20) and (21) with associated connecting lead (40), (43) are inserted via lumen (8) and guided through valve (10) (not shown) and piston (12) (not shown). In doing so, the screw-in electrodes are guided through the myocardium of the right ventricle and further on through the ventricle septum. The screw-in electrode poles may be fixed in the endocardium of the left ventricle. The screw-in electrode poles (20), (21) are connected to the impedance detecting unit (80) via connecting leads (40), (41). The proximally placed disc (4) of the nitinol mesh of said monitoring and regulation device is connected to the impedance detecting unit (80) via connecting lead (41). The whole nitinol mesh is thus forming the indifferent pole (23). The electrical field lines during impedance measurement are marked in FIG. 4

For resistance measurement a sinusoidal alternating current of more than 10 kHz is made to flow between pole (23) and the poles (20) and (21), said poles (20) and (21) being switched parallel. The current intensity is about 3-5 mA.

Figure 5:
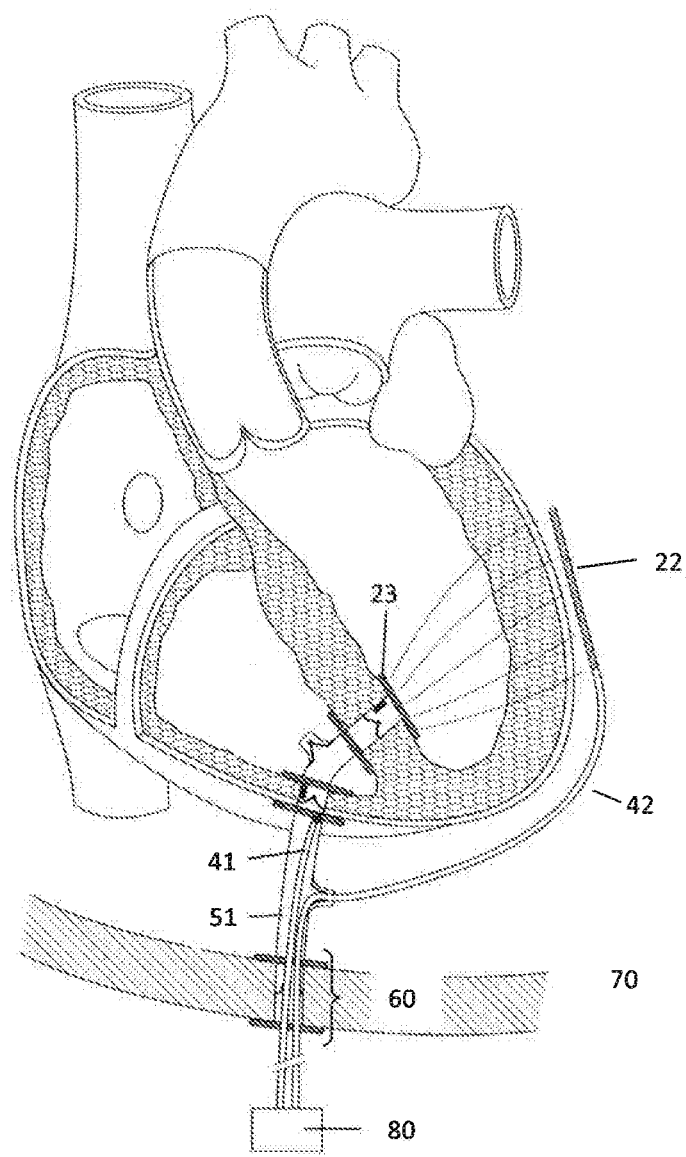

FIG. 5 shows the monitoring and regulation device being implanted in the heart. The device shown in FIG. 5 may also be used for impedance measurement. A coil shaped electrode pole (22) is placed beyond the heart in the chest cavity. Electrode pole (22) is connected to the impedance detecting unit (80) via connecting lead (42). The nitinol mesh forming a pole (23) is connected to the impedance detecting unit (80) via connecting lead (41). For resistance measurement a sinusoidal alternating current of more than 10 kHz is made to flow between pole (23) and the pole (22). The current intensity is about 3-5 mA.

The impedance detecting unit (80) is placed extracorporeally. The connecting leads (41) and (42) to the poles (22) and (23) are guided through the abdominal wall (70) by means of the introduction device (60), said device (60) being connected to the monitoring and regulation device by shaft (51). The introduction device (60) may be a braiding of nitinol wires and corresponds to the proximal part of the monitoring and regulation device with disc shaped sections (3) and (4). Shown in FIG. 1a, 1b. Shaft (51) has an opening for the connecting lead (42).

Figure 6:
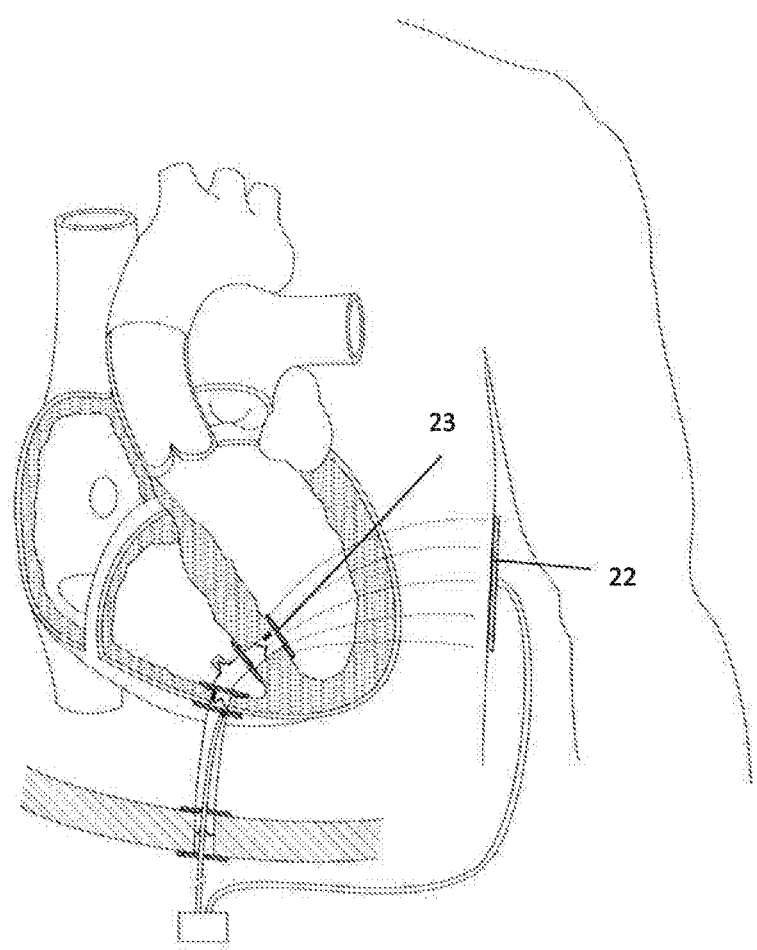

Electrode pole (22) may also be attached beyond the chest cavity as shown in FIG. 6.

The invention claimed is:

1. A monitoring and regulation device configured for implantation in a heart comprising:
at least one pressure sensor being located in a distally arranged section of a shaft, the pressure sensor being configured to output data that is used to monitor vital parameters of a cardiovascular system;
the regulation device configured for regulating blood flow and blood pressure, the regulation device comprising:
the shaft, the shaft being tubular and fluid-tight and having a lumen extending axially there through, the shaft having distal and proximal sections and a central section, wherein the distal and proximal sections are disc-shaped extended thus forming a first double disc at the distal section and a second double disc at the proximal section, the central section linking the first and second double discs, the central section of the shaft having an opening, a length of the central section being adapted to an anatomical characteristic of a right ventricle of the heart, said length corresponding to a distance between a myocardium wall of the right ventricle and a right ventricle septum of the heart;
a first pressure valve disposed in the opening in the central section of the shaft;
a second pressure valve located in the lumen in the proximal section of the shaft; and
a sliding element housed inside the lumen, the sliding element having an axially movable and rotatable cylindrical piston and a piston rod, wherein pushing the piston towards the distal section of the shaft or rotating the piston results in a partially or completely closing of the opening to control the blood flow.

2. The monitoring and regulation device according to claim 1, wherein the shaft includes a braiding or mesh of nitinol wires and the shaft is coated by a fluid tight material.

3. The monitoring and regulation device according to claim 2, wherein the fluid tight material is silicone.

4. The monitoring and regulation device according to claim 1, wherein said piston is equipped with a sensor.

5. The monitoring and regulation device according to claim 1, wherein said piston has a raked surface at its distal end.

6. The monitoring and regulation device according to claim 2, wherein the shaft includes the mesh of nitinol wires, the monitoring and regulation device further comprising at least one stimulating electrode pole being connected to a pacemaker via a connecting lead, said stimulating electrode pole and the connecting lead being configured to be guided via the shaft into a left ventricle of the heart, and wherein the mesh of nitinol wires of the monitoring and regulating device is connected to the pacemaker via the connecting lead such that the mesh of nitinol wires forms an indifferent pole.

7. The monitoring and regulation device according to claim 2, wherein the shaft includes the mesh of nitinol wires, the monitoring and regulation device further comprising at least one electrode being connected via a connecting a lead to at least one electrode that is configured to measure cardiac impedance, and wherein the mesh of nitinol wires is connected via the connector lead to the at least one electrode such that the mesh of nitinol wires forms an electrical pole.

* * * * *